United States Patent [19]

Kebabian

[11] Patent Number: 4,605,313
[45] Date of Patent: Aug. 12, 1986

[54] INFRARED DETECTOR FOR NDIR GAS ANALYSIS

[75] Inventor: Paul L. Kebabian, Acton, Mass.

[73] Assignee: Environmental Research & Technology, Inc., Concord, Mass.

[21] Appl. No.: 721,601

[22] Filed: Apr. 10, 1985

[51] Int. Cl.⁴ .............................. G01J 5/00
[52] U.S. Cl. .................. 374/121; 374/123; 250/343
[58] Field of Search ............... 374/121, 123; 250/343

[56] References Cited

U.S. PATENT DOCUMENTS

| | | | |
|---|---|---|---|
| 2,327,539 | 8/1943 | McAlister | 250/343 |
| 2,534,657 | 12/1950 | Bray | 250/343 |
| 2,938,117 | 5/1960 | Schmidt | 250/343 |
| 3,391,278 | 7/1968 | Duepner | 250/343 |
| 3,588,497 | 6/1971 | Jordan | 250/343 |
| 3,809,920 | 5/1974 | Cohen et al. | 374/121 |
| 3,911,277 | 10/1975 | Cederstrand et al. | 374/123 |
| 4,105,919 | 8/1978 | Bridges et al. | 250/343 |
| 4,177,381 | 12/1979 | McClatchie et al. | 250/343 |
| 4,205,913 | 6/1980 | Ehrfeld et al. | 250/343 |
| 4,271,124 | 6/1981 | Speeter | 250/343 |

FOREIGN PATENT DOCUMENTS 0642750  9/1950  United Kingdom ............... 250/343

Primary Examiner—Charles Frankfort
Assistant Examiner—Thomas B. Will
Attorney, Agent, or Firm—Sughrue, Mion, Zinn, Macpeak, and Seas

[57] ABSTRACT

A detector for a gas analyzer includes a thermal detector, an absorptive film on the surface of said thermal detector, and an enclosure containing a reference gas of the gas species of interest such that the thermal detector is in thermal contact with both the absorptive film and the reference gas. During irradiation, the absorptive film absorbs radiation which passes through the reference gas and causes the thermal detector to generate a corresponding output. When the irradiation is terminated, the heat content of the reference gas, which will be dependent upon the amount of the radiation absorbed, will be communicated to the thermal detector to cause the thermal detector to provide a second output representing the amount of radiation absorbed by the reference gas.

15 Claims, 21 Drawing Figures

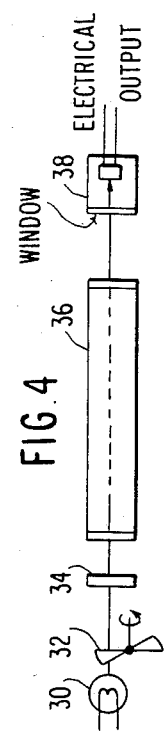
FIG. 2a PRIOR ART
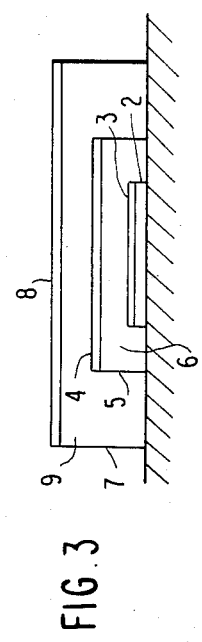
FIG. 2b PRIOR ART
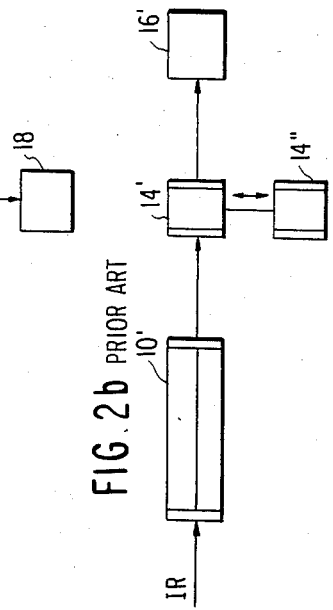
FIG. 3
FIG. 4
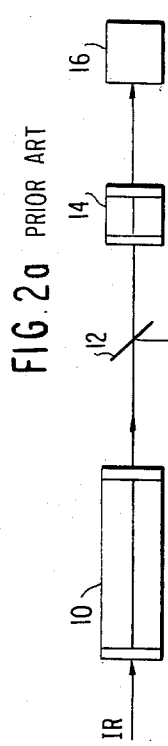
FIG. 1a
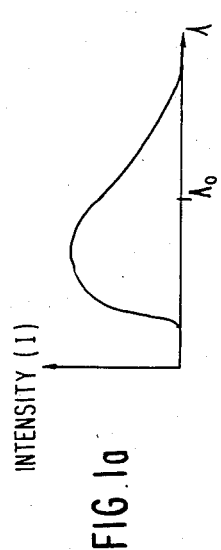
FIG. 1b
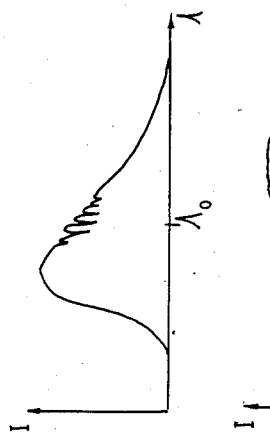
FIG. 1c
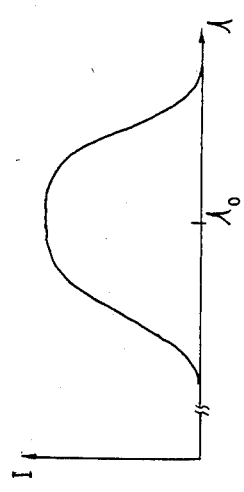
FIG. 1d
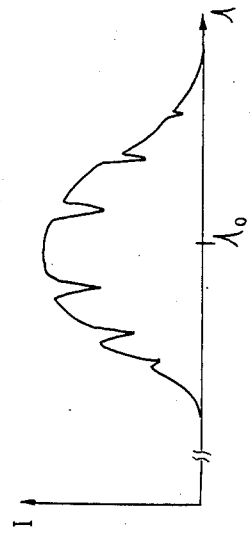

FIG. 5
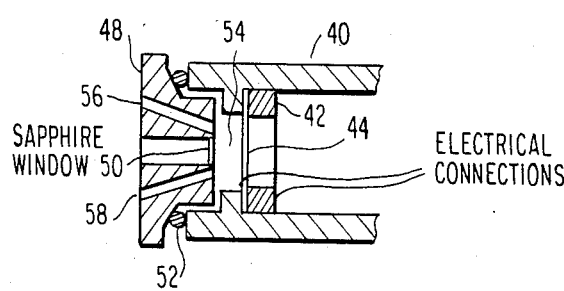
FIG. 6
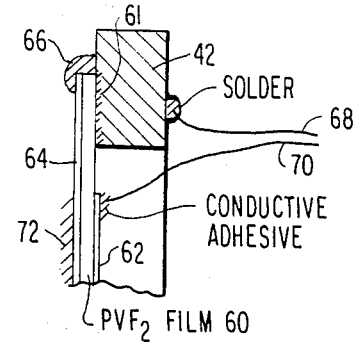
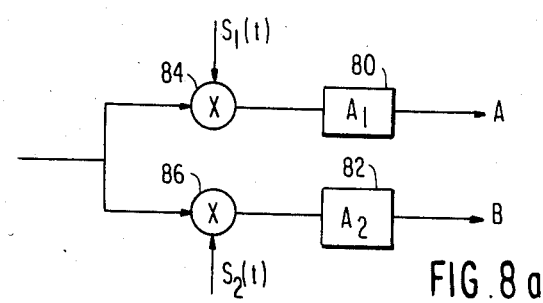
FIG. 8a
FIG. 8b
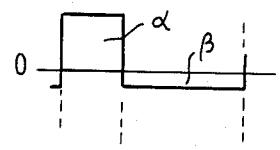
FIG. 8c
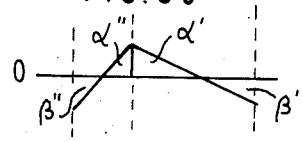
FIG. 8d
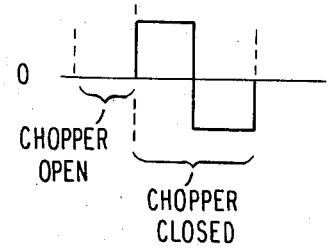
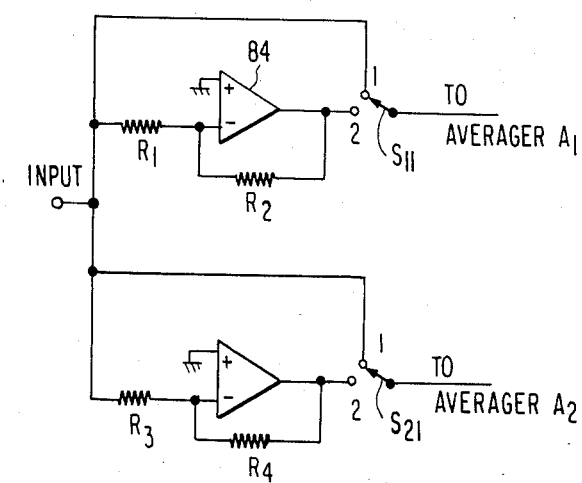
FIG. 8e

INFRARED DETECTOR FOR NDIR GAS ANALYSIS

BACKGROUND OF THE INVENTION

This invention relates to a gas analyzer, and more particularly to an analyzer for detecting the concentration of a particular gas in a gas sample in accordance with the absorption spectrum of the gas sample. The invention will be described in the context of infrared (IR) gas analysis, although the principles of the invention are equally applicable to other optical analyzer.

It is well-known that any particular gas will absorb light in discrete portions of the spectrum. Thus, a gas can be analyzed by passing light through the gas and examining the spectral "signature". For example, a broadband source having an intensity distribution as generally illustrated in FIG. 1a may be passed through a sample of gas having many discrete absorption lines, with the detected radiation on the other side of the gas sample being generally as illustrated in FIG. 1b. When analyzing a gas sample to detect the presence of a particular gas, some form of filter would normally be used to limit the broadband radiation from a thermal source to the part of the spectrum, e.g., a particular part of the IR spectrum, in which that particular gas has its absorption lines. Thus, after filtering, the spectrum of FIG. 1a would appear as in FIG. 1c limited to a band around $\lambda_0$ where the gas species of interest has its absorption lines, and the absorption spectrum in FIG. 1b would then appear as in FIG. 1d. The concentration of the particular gas can then be determined in accordance with the amount of light absorbed.

Ideally, one would detect separately, i.e., discriminate between, light in the vicinity of the absorption lines and rest of the IR light. The ratio between these two amounts of light would vary with absorption by the gas of interest. Interferents would tend to absorb both ranges of light equally, thus leaving the ratio unchanged. Naturally, this interference rejection is only approximate, and the changes in the spectral shape of the source could also influence the ratio to some extent.

Prior art NDIR (Non-Dispersive InfraRed) gas analyzers have not been able to directly implement this separate detection of the two parts of the spectrum in the manner described above. Instead, most methods involved operations designed to measure the total light passing through the sample and the light passing through the sample in the spectrum outside of the absorption lines. These two signals must then be subtracted to obtain the light in the vicinity of the absorption lines. For example, in the technique briefly illustrated in FIG. 2a, IR radiation passes through an absorption cell 10 containing the gas to be analyzed and then passed through a beam splitter 12 to a reference cell 14 containing a sample of the gas species of interest. The reference cell 14 contains enough of the species of interest that most of the light in the vicinity of the absorption lines is absorbed. A reference detector 16 will then detect the radiation passing through the reference cell and will provide an output signal proportional to the part of the light flux, exiting absorption cell 10, that is remote from the absorption lines. The light flux exiting the absorption cell 10 is also reflected by the beam splitter 12 to a signal detector 18 which will provide an output signal proportional to the total flux exiting the absorption cell 10.

In principle, for the analyzer shown in FIG. 2a, one could put enough of the gas species of interest into the absorption cell 10 that most of the light in the vicinity of the absorption lines would be absorbed, and then adjust the responsivity of one of the detectors so that their outputs were equal. The difference in the output signals from the two detectors would then be proportional to the light flux in the vicinity of the absorption lines, while the signal from the detector 16 would be porportional to the light outside of the absorption lines. In practical NDIR gas analyzers, an equivalent balancing of the detector responsivities usually is performed differently, but the above-described balance method illustrates the principle involved.

In an alternate arrangement shown in FIG. 2b, the reference cell 14' is moveable into and out of the path of the light flux between the absorption cell 10' and the detector 16'. With the reference cell 14' in the path of the light flux, the detector 16' would provide an output signal corresponding to the output signal from the detector 16 in FIG. 2a. With the empty cell 14" in the path of the light flux, the detector 16' would provide an output signal corresponding to the output signal from the signal detector 18 in FIG. 2a.

In either of the above techniques, the quantity of interest is the ratio of flux in the vicinity of the absorption lines to flux outside the absorption lines. Therefore, broadband absorption by the gas to be analyzed in absorption cell 10 will not change that ratio, nor will changes in the output of the infrared source. Similarly, when the gas in the absorption cell 10 has a line-type absorption spectrum, different from that of the species of interest, then on the average the two signals will be reduced proportionally. This last property is statistical—there is no guarantee that, for an especially ill-chosen filter passband (see FIGS. 1a–1d), a line-spectrum-absorbing interferent may not cause a change in the ratio of the two signals. However, in practice a very high degree of interference rejection is usually obtained.

Some disadvantages of the prior art NDIR gas analyzers are that, for those similar to the type illustrated in FIG. 2a, two detectors are required, and the responsivities must be kept properly balanced. The need for a beam splitter further complicates the optical layout. For the case of FIG. 2b, the moveable cells are relatively expensive to fabricate, requiring a drive motor, bearings, etc., all of which also tend to make the system less reliable.

A further type of known NDIR gas analyzer is the Luft cell. This device measures only the intensity of the light in the vicinity of the absorption lines, and thus other means of inteference rejection must be employed. Luft cell detectors are also relatively complex and expensive to manufacture.

SUMMARY OF THE INVENTION

It is an object of this invention to provide a gas analyzer which does not require the use of a reference detector. It is a further object of this invention to provide such an analyzer which is less complex and costly than the conventional analyzers discussed above.

It is a still further object of this invention to provide a gas analyzer which is capable of directly implementing the separate detections of the light in the vicinity of the absorption lines and the remaining light.

Briefly, these and other objects are achieved according to the present invention by a gas analyzer which includes a thermal detector, e.g., a pyroelectric detector, having an absorptive coating, with a sample of the gas species of interest, i.e., the reference gas, being in substantially direct contact with the thermal detector. Light passing through the gas will be absorbed in the absorption spectra, with the remaining light striking the absorptive surface coating. This generates heat in the absorptive surface coating, thereby resulting in an output from the thermal detector corresponding to the amount of light outside of the absorption lines. The radiation source is pulsed, and when the pulse is turned off, the generation of heat in the absorptive surface coating will terminate. However, the light absorbed by the sample gas during the "on" period of the radiation source will have resulted in heating of the reference gas. During the "off" period of the radiation source, the heat from the reference gas will be transmitted to the thermal detector, causing the signal from the thermal detector to decay gradually rather than terminate abruptly when the light source is turned off. The amount of heat in the reference gas, and consequently the amplitude of the gradually decaying signal from the thermal detector during the "off" period of the radiation source, will be dependent on the amount of light absorbed by the reference gas.

The detector of this invention is therefore capable of directly detecting the absorbed light and the non-absorbed light, and does so using a single detector without the necessity of a complex mechanical arrangement.

BRIEF DESCRIPTION OF THE DRAWINGS

The invention will be more clearly understood from he following description in conjunction with the accompanying drawings, wherein:

FIG. 1a illustrates the intensity distribution of a broadband radiation source;

FIG. 1b illustrates portions of the radiation of FIG. 1 absorbed by a gas of interest;

FIGS. 1c and 1d correspond to FIGS. 1a and 1b, respectively, after filtering to a band around wavelength $\lambda_0$ where the gas species of interest has absorption lines;

FIGS. 2a and 2b are explanatory diagrams of conventional NDIR gas analyzers;

FIG. 3 is a side sectional view of one example of a detector according to the present invention;

FIG. 4 is an explanatory diagram of a typical operating configuration of a gas analyzer using the detector of the present invention;

FIG. 5 is a side sectional view of a further example of a detector according to the present invention;

FIG. 6 is an illustration of a pyroelectric detector construction as used in the arrangement of FIG. 4;

FIG. 8a is a general illustration of signal processing circuit for processing the output signal from the detector;

FIGS. 8b-8d show relevant waveforms, in idealized form, for explaining the operation of the signal processing circuitry of FIG. 8a;

FIG. 8e is an expanded diagram of a portion of the signal processing circuitry of FIG. 8a.

DETAILED DESCRIPTION OF THE INVENTION

Figure 7A:
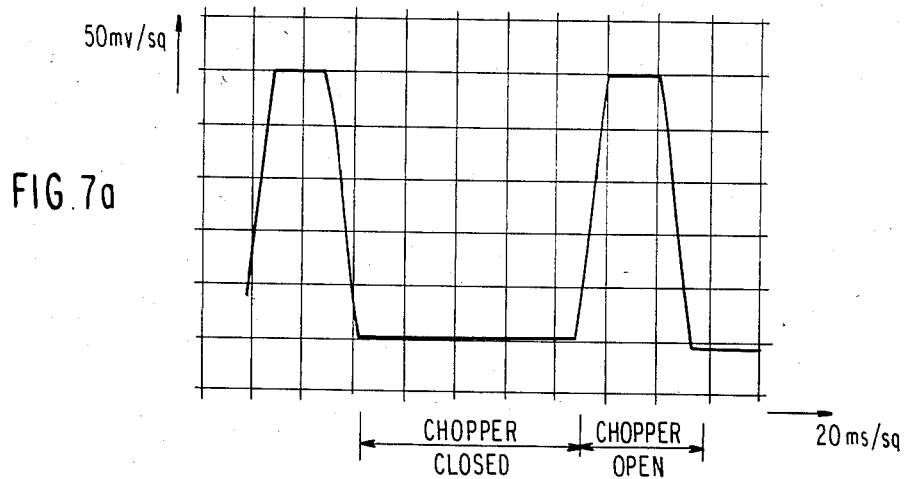
FIGS. 7a-7c are illustrations of waveforms for explaining the operation of the detector of FIG. 4.

The present invention comprises a single detector for implementing the required separate detection of light in the vicinity of and remote from the absorption lines of the gas to be detected. The basic structure of the detector of this invention is shown in FIG. 3. As shown in this figure, a substrate 1 supports a thermal detector 2, e.g., a pyroelectric detector. An absorptive coating 3 is provided on the surface of the termal detector 2. The detector is enclosed by a window 4 which is transparent to the radiation source being used, the window 4 being supported by a window support 5. In the enclosure defined by the window 4 and the window support 5, the reference gas 6 is contained. Since the thermal detector may be any of several types currently used for infrared detection, details of its construction such as thermal insulation from the substrate, electrical connections, etc., are not shown in the figure.

The inner enclosure is surrounded by an outer enclosure comprising an outer window support 7 and an outer window 8. A medium 9 of low thermal conductivity, such as a dense gas, is contained within the space defined by the inner and outer enclosures, or the outer enclosure may be evacuated. Both windows 4 and 8 as well as the medium 9 must transmit light in that part of the radiation spectrum being used for detection purposes.

The detector illustrated in FIG. 3 is used with a source of radiation that is chopped into a train of pulses and is preferably limited by a suitable filter to a range of the spectrum in which the gas of interest exhibits it greatest absorption characteristics. When a pulse of radiation from the source enters the detector and passes through the reference gas 6 of the gas species of interest, the part of the light remote from the absorption lines will strike the absorptive surface coating 3 and will result in some degree of heating of the thermal detector 2, thereby providing an output representing the amount of light outside of the absorption lines. Assuming that the column density of the reference gas 6 (i.e., the product of its concentration times the spacing between the absorptive surface 3 in the inner window 4) is sufficiently large, most of the light in the vicinity of the absorption lines will not reach the absorptive surface coating 3 but will instead be absorbed in the reference gas 6, thus heating that gas. After the end of the radiation pulse, the heat from the reference gas 6 will be at least partially conducted to the detector 2, thus creating a further detection signal which is separated in time from the detection signal produced by the light incident on the absorptive surface coating 3.

Assuming that the spacing from the detector 2 to the window 4 is small compared to the width of the detector, most of the heat generated in the reference gas 6 by absorbing the radiation in the vicinity of the absorption lines will flow to either the window 4 or the detector 2. It would be desirable to ensure that as much as this heat as possible flow to the detector 2, and for this reason the window 4 should be thin and have a low heat capacity, while the medium 9 should provide as much thermal insulation as possible. For most practical purposes, the above requirement means that the heat capacity of the window 4 must be smaller than that of the detector itself, and this in turn generally means that the window 4 must be quite thin. For example, a typical pyroelectric detector is made from poly-vinyldienefluoride ($PVF_2$)

film approximately 9μ thick. Where such a window is impractical, then heat conducted to it will be lost, and in that case the outer window 8 and insulating medium 9 serve no purpose and may be eliminated.

In some circumstances, such as when the reference gas 6 consists of carbon monoxide of very high purity, the energy absorbed in the reference gas 6 will flow to the detector 2 and the window 4 by diffusion of vibrationally excited atoms, rather than as heat. However, this difference will not change the time-multiplex nature of the signal output from the detector 2.

A specific example of the design and operation of the present invention will now be described with reference to FIGS. 4-7. The overall design of a typical operating configuration of the invention is shown in FIG. 4. Light from an infrared radiation source 30, e.g., a heated filament, is chopped by a rotating shutter 32 and then passes through a bandpass filter 34 and a light-pipe absorption cell 36 containing the gas to be analyzed. By way of example, the cell 36 may be ten inches in length, and the filter passband may be centered around 4.3μ where carbon dioxide ($CO_2$) absorbs strongly at a large number of discrete absorption lines. The light flux exiting the absorption cell 36 is then detected by a time-multiplexed detector 38.

A time-multiplexed detector was constructed in substantially the form illustrated in FIG. 5, wherein a housing 40 contained a mounting ring 42 for supporting a $PVF_2$ film pyroelectric element 44. A cap 48 having a sapphire window 50, which cap is sealed at the end of the housing via an O-ring 52, resulting in an enclosure 54 immediately above the pyroelectric element 44. The cap 48 included a gas inlet hole 56 and a gas outlet 58. These permitted the region 54 to be filled with $CO_2$, and maintained filled despite leakage around the detector.

The pyroelectric detector 44 illustrated in FIG. 5 was made of a $PVF_2$ film with an absorptive surface applied to it. Although some absorption occurs in the film itself, especially at longer wavelengths than are used here, when metallic electrodes are used they reflect the incident radiation before it can be absorbed. The pyroelectric detector element may be a conventional, commercially available, pyroelectric detector having a detailed structure as shown in FIG. 6, with the $PVF_2$ film 60 mounted to the mounting ring 42 by means of an adhesive 61. Inner and outer electrodes 62 and 64, preferably, metallic electrodes, would be in contact with opposite surfaces of the $PVF_2$ film 60, with a conductive paint 66 electrically connecting the outer electrode to the mounting ring 42. A lead wire 68 could be soldered to the rear surface of the mounting ring 42 to thereby couple to the outer electrode 64, and a lead wire 70 could be secured by a conductive adhesive to the inner electrode 62. An absorptive coating 72 would be deposited on the surface of the outer electrode directed toward the source of light flux. The various features illustrated in FIG. 6, and any remaining details necessary for the implementation of a pyroelectric detector element, would be well-known to those of skilled in the art.

Figure 7B:
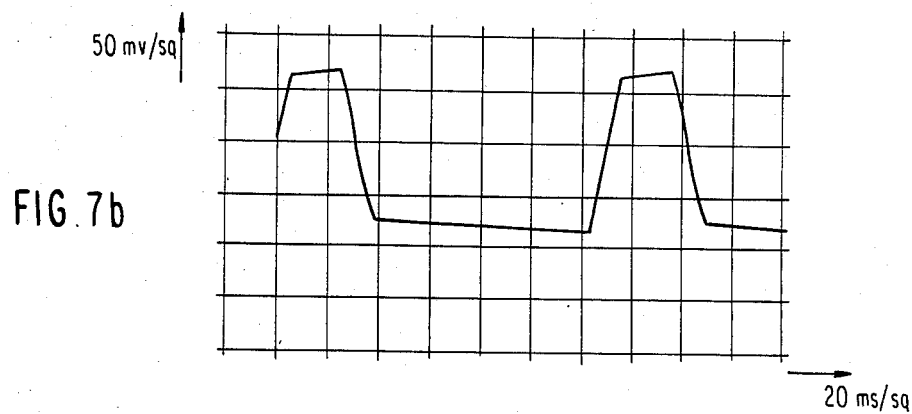
Figure 7C:
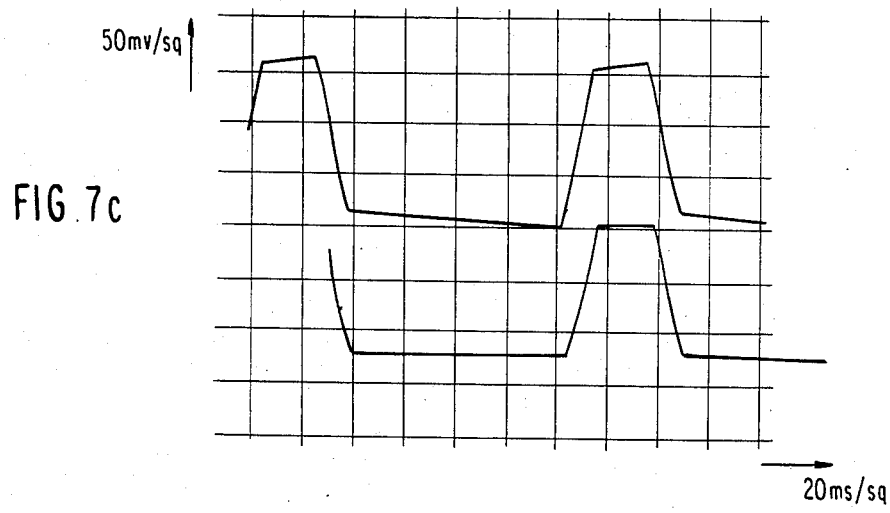

The scope waveforms of FIGS. 7a-7c illustrate the functioning of this detector. FIG. 7a shows a signal porportional to the current from he pyroelectric detector, which is in turn porportional to the thermal power input to the detector. In this case, there was no $CO_2$ in either the absorption cell 36 in FIG. 4 nor in the reference cell 54 of the detector in FIG. 5. While the chopper is open, the detector is heated, resulting in a positive detector output signal. While the chopper is closed, the detector cools, resulting in a negative detector output signal. Because the chopping period is an appreciable fraction of the thermal time constant between the detector and its environment, the rate of cooling gradually decreases, and this appears as the small upward slope seen in the chopper-closed phase in FIG. 7a.

FIG. 7b shows the detector output signal when a $CO_2$ reference gas has been added to the reference cell 54 in the detector of FIG. 5. The amplitude of the signal in the chopper-open phase is smaller, because only that part of the IR flux outside of the absorption lines of the $CO_2$ reaches the detector. Note that during the chopper-open phase, the signal shows a steady increase in the middle part of the phase, where the signal in the chopper-open phase illustrated in FIG. 7a was substantially constant. This is the result of the gradual heating of the reference gas. After the chopper closes, the signal shows a downward slope resulting from the heat from the $CO_2$ flowing into the detector. As this happens, the temperature of the gas cools to closer to the temperature of the detector film, and thus the thermal power input from the gas to the detector decreases, causing the downward slope of the signal.

FIG. 7c illustrates the effect of adding 1% $CO_2$ to the absorption cell. The upper trace is the signal before adding the $CO_2$ while the lower trace is afterwards. Note that the signal during the chopper-closed phase has been eliminated, because the relatively large column density in the absorption cell has removed the light in the vicinity of the absorption lines before it reaches the detector or reference gas.

The signal from the detector may be processed by synchronous demodulation, a technique well known in the signal processing art. The signal processing configuration may be as shown in FIG. 8a, while FIGS. 8b-8d show the relevant waveforms, in idealized form.

A pyroelectric detector inherently produces a current proportional to the rate to change of its temperature, i.e., to the thermal power input. Thus, in steady state operation its output has zero average value. The component of the signal caused by the IR flux away from the absorption lines of the reference gas is shown in FIG. 8b. Because this signal must have zero average value, the areas denoted α and β in the figure are equal and opposite. While the chopper is open, the reference gas is being heated, and while it is closed the reference gas cools. The resulting component of the signal is shown in FIG. 8c. Because the average value must be zero, the areas under this waveform have the relation $\beta' = -\alpha'$ and $\beta'' = -\alpha''$.

As can been seen from an inspection of FIGS. 8a-8c, the average value of the product of the signals of FIGS. 8a and 8b is identically zero, while the average value of each of these signals squared is non-zero, therefore, one may choose demodulation waveform $s_1(t)$ to have some arbitrary (fixed) amplitude and a shape proportional to that shown in FIG. 8b. Similarly, demodulation waveform $s_2(t)$ has a fixed amplitude and a shape proportional to that shown in FIG. 8c. With this choice of $s_1(t)$ and $s_2(t)$, the output A of the averaging circuit 80 in FIG. 8a is proportional to the IR flux away from the absorption lines of the reference gas, while the output B of the averaging circuit 82 in FIG. 8a is proportional to the IR flux in the vicinity of the absorption lines.

In implementing this signal processing arrangement, it is advantageous that the demodulating waveforms should assume only two discrete values. Waveform $s_1$ meets this requirement, but $s_2$ does not. FIG. 8d shows a 2-valued demodulating waveform that also results in an output proportional to the IR flux absorbed by the reference gas, and independent of that not absorbed by the reference gas. In this case, $\beta''' = -\alpha'''$.

The demodulating waveforms are synchronized to the chopper. FIG. 8e is an example of how these waveforms, and the corresponding multipliers 84 and 86, may be realized using an operational amplifier and a switch. The averaging circuits would be conventional lowpass filters. Switch $S_{11}$ is in position 1 while the chopper is open, and is in position 2 while the chopper is closed. With open and closed durations of $t_1$ and $t_2$, respectively, the gain of the inverting amplifier, which is equal to $-R_1/R_2$, is selected according to the relation $R_1/R_2 = t_2/t_1$.

Switch $S_{21}$ is in its position 1 during the first half of the chopper-closed phase, and is in its position 2 during the second half of the chopper-closed phase. In this case $R_4 = R_3$.

Thus, as can be seen from the above description, the signal may be processed by very simple circuitry to obtain measurements of the flux within, and away from, the absorption lines of the reference gas. Naturally, other signal processing methods besides those described above could be used. For example, the output of the detector could be digitized, and the synchronous demodulation could be implemented as a digital algorithm. The description above is not presented in any limiting sense, but only to illustrate, that, if desired, the signal processing may be done in a very straightforward manner.

In certain critical applications, two other small effects need be considered. Even at the centers of the absorption lines, some the incident light is transmitted through the reference gas, and during the chopper-open phase, some heat conducts from the surface of the pyroelectric detector to the adjacent reference gas. Thus, a slight degree of cross-coupling exists between the near-lines and the away-from-lines signals. Where this effect is significant, it can be corrected by subtracting the appropriate, small, fraction of each of the raw signals (e.g., A and B in FIG. 8a) from the other, by electrical or other means.

It can be seen from the above description that the detector of the present invention provides a simple and effective means for directly measuring absorbed and non-absorbed radiation, resulting in a detector of improved reliability and accuracy and decreased complexity and cost.

Figure 9A:
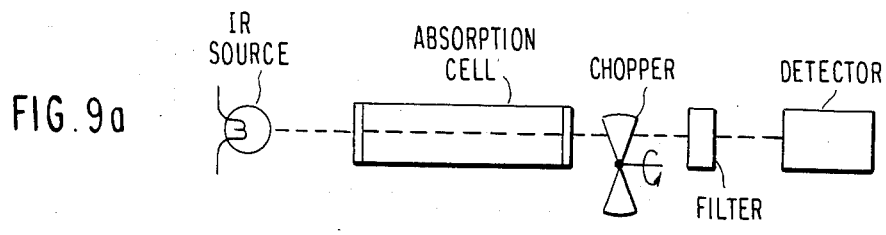
FIGS. 9a-9c are diagram illustrating alternative arrangements for the detector of the present invention.
Figure 9B:
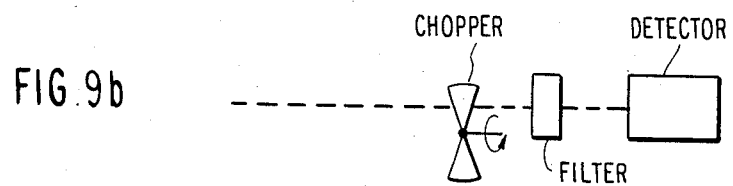
Figure 9C:
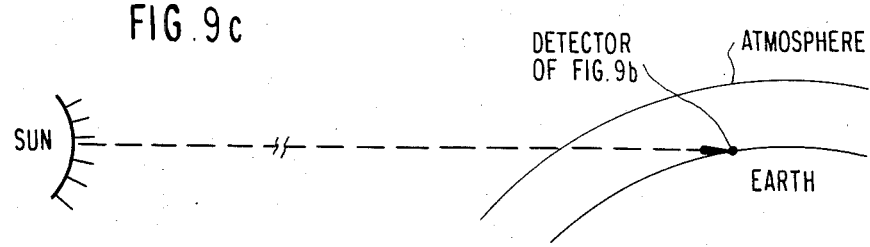

In the description above, the detector of the present invention has been used in conjunction with a local source IR radiation and an absorption cell containing the gas to be analyzed. However, the present invention may be used in any application where one wishes to measure the relative fluxes of radiation in the vicinity of, and remote from, the absorption lines of the reference gas. For example, FIG. 9a illustrates the configuration of FIG. 4 modified by moving the chopper and filter to directly in front of the detector. Obviously, this functions exactly the same way as the apparatus shown in FIG. 4. However, the incident radiation may now be from any source whatever and not just the radiation from a local source transmitted through a local absorption cell. This is illustrated in FIG. 9b. An example of this mode of operation is shown in FIG. 9c, where the source of radiation is the sun and the gas to be analyzed is a column through the earth's atmosphere. Such an apparatus would be of great use in the remote measurement of air pollutants, for example.

It should be noted that, while the present invention has been described above in the context of IR detector of $CO_2$, the invention could be used to detect any gas having an absorption spectrum consisting of discrete lines. Further, it should be noted that the detector is not limited to use with only IR radiation, but can be used with other types of radiation as well. For example, many gases have a line absorption spectrum for ultraviolet light, and the technique of the present invention could be implemented for ultraviolet radiation, since the thermal detector can respond to ultraviolet as well as infrared radiation.

Further changes and modifications could be made in the embodiment described above without departing from the spirit and scope of the invention. For example, the absorptive coating 3 may be selected to be less than fully absorptive, or even only very slightly absorptive. The reason for such a modification would be that, in many cases of practical interest, the absorption lines are narrow compared to their spacing. By making the coating 3 only partly absorptive, the time-multiplex signals generated by the detector would be made more nearly equal, thus simplifying the requirements placed on the circuitry that subsequently processes those signals.

What is claimed:

1. A detector for receiving radiation and providing a first signal in accordance with the amount of said radiation absorbed by a reference gas and a second signal in accordance with the amount of said radiation not substantially absorbed by said reference gas, said detector comprising:
    a first enclosure containing said reference gas, and being at least partially transparent to said radiation;
    absorption means for absorbing radiation which passes through said reference gas without absorption by said reference gas; and
    a thermal detector, in thermal contact with said absorption means and said reference gas, for providing an output signal responsive to the temperature of said thermal detector, said output signal being alternatively indicative of said first or said second signal.

2. A detector as defined in claim 1, wherein said thermal detector is a pyroelectric detector.

3. A detector as defined in claim 2, wherein said absorption means comprises an absorptive film on a surface of said pyroelectric detector.

4. A detector as defined in claim 1, further comprising a second enclosure surrounding said first enclosure and containing a medium of low thermal conductivity, said second enclosure being at least partially transparent to said radiation and said medium of low thermal conductivity being substantially transparent to said radiation.

5. A detector as defined in claim 4, wherein said low thermal conductivity medium comprises a dense gas.

6. A detector as defined in claim 1, further comprising a second enclosure surrounding said first enclosure and being maintained at vacuum, said second enclosure being at least partially transparent to said radiation.

7. A detector as defined in claim 1, further comprising means responsive to said output signal from said thermal detector for providing said first and second signals in accordance with the temporal behavior of said thermal detector output signal.

8. A gas analyzer for measuring the concentration of a particular gas species in a sample, said particular gas species having an absorption spectrum, said concentration measurement being made by measurement of the absorption by said particular gas species of radiation in the vicinity of, and away from, said absorption spectrum, said gas analyzer comprising:

radiation means for directing radiation through said sample;

a first enclosure, at least partially transparent to said radiation and containing a reference gas of said particular gas species, for receiving radiation passed through said gas sample;

absorption means for absorbing radiation which passes through said reference gas; and a thermal detector, in thermal contact with said absorption means and said reference gas, for providing an output signal responsive to the temperature of said thermal detector, said output signal being alternatively indicative of the measurement of the absorption by said reference gas of radiation in the vicinity of said absorption spectrum or a measurement of the radiation which passes through said reference gas, said output signals being used to measure the concentration of said particular gas species in said sample.

9. A gas analyzer as defined in claim 8, werein said radiation means comprises a pulsed radiation source.

10. An analyzer as defined in claim 8, wherein said radiation source emits continuously, said analyzer further comprising a chopper for periodically interrupting the radiation between said radiation means and said detector.

11. A gas analyzer as defined in claim 8, wherein said radiation comprises infrared radiation.

12. An analyzer as defined in claim 8, wherein said absorption means comprises a film on a surface of said thermal detector.

13. An analyzer as defined in claim 8, wherein said absorption spectrum consists of narrow lines.

14. A gas analyzer as defined in claim 8, wherein said radiation is intermittent with on and off periods, said thermal detector providing an output signal during said on period which is representative of the amount of light absorbed by said absorption means, and said thermal detector providing an output signal during said off period which is representative of the amount of radiation absorbed by said reference gas.

15. A gas analyzer as defined in claim 8, further comprising means responsive to said thermal detector output signal for determining the concentration of said particular gas species in accordance with the temporal behavior of said thermal detector output signal.

* * * * *